United States Patent [19]

Rabban

[11] 4,116,232

[45] Sep. 26, 1978

[54] SURGICAL RETRACTOR

[76] Inventor: Philipp Rabban, P.O. Box 390942, Miami Beach, Fla. 33139

[21] Appl. No.: 775,137

[22] Filed: Mar. 7, 1977

[51] Int. Cl.² .............................................. A61B 17/02
[52] U.S. Cl. .................................................... 128/20
[58] Field of Search ................................ 128/13–19, 128/20

[56] References Cited

U.S. PATENT DOCUMENTS

| 516,842 | 3/1894 | Scheerer | 128/20 |
| 2,354,471 | 6/1944 | Macintosh | 128/10 |
| 3,724,449 | 4/1973 | Gauthier | 128/20 |
| 3,749,088 | 7/1973 | Gauthier | 128/20 |
| 4,010,741 | 3/1977 | Gauthier | 128/20 |

FOREIGN PATENT DOCUMENTS 474,479  4/1929  Fed. Rep. of Germany ............. 128/20

Primary Examiner—Robert W. Michell
Assistant Examiner—Henry S. Layton
Attorney, Agent, or Firm—C. Bruce Hamburg

[57] ABSTRACT

A surgical retractor according to the invention comprises a straight shaft, a blade and means for pivotally connecting the blade to the shaft with the blade oriented perpendicularly to the shaft and being free to turn about an axis perpendicular to the shaft. The retractor may further comprise means for telescopically adjusting the length of the shaft and releasably fixing the shaft at the adjusted length. A sole may be formed on the free extremity of the blade most remote from the pivotal connection, the sole being symmetrically formed on the blade and defining surfaces in planes perpendicular to the turning axis of the blade, the surfaces extending equally beyond the thickness of the blade in opposite directions.

5 Claims, 2 Drawing Figures

SURGICAL RETRACTOR

BACKGROUND OF THE INVENTION

This invention relates to an improved surgical retractor. More particularly, this invention relates to an improved surgical retractor especially useful during the closure of a surgical incision.

Presently, the retraction of the sides and angles of a surgical incision during the closure procedure is performed by the operator himself, by the first assistant or by the second assistant, all using a conventional retractor or their fingers or by means of a self-retaining retractor. Such present practices are inefficient, inaccurate and even too traumatic and hazardous. Moreover, when there is a second assistant who is assigned the task of retracting the incision during the closure procedure in a lengthy operation in order to try to hasten the completion of the operation, his hands are the fifth and sixth involved in the operation and are frequently too close to the incision, impairing free access to the incision and the motions of the surgeon as well as those of the patient's respiration. On the other hand, self-retaining retractors are too rigid. They evenly stretch opposite sides of the incision, causing unnecessary trauma and not adapting to continuously changing needs during the closure of the incision. For example, neither the anatomy along the incision nor the motions of the surgeon are uniform. Since static retraction is quite unsuitable for the closure of an incision, the positioning and stressing exerted by a self-retaining retractor must be changed with inconvenient frequency. Even then, at any given moment the self-retaining retractor is to some extent retracting where retraction is not needed and, thus, causing unnecessary trauma while to some extent not retracting exactly where retraction is needed.

It is an object of the invention to provide an improved surgical retractor, designed to be especially useful during the closure of a surgical incision, which avoids the disadvantages of the prior retractors and practices.

Other objects and advantages of the invention will be apparent to one skilled in the art from the following description of the invention.

SUMMARY OF THE INVENTION

According to the invention, there is provided an improved surgical retractor especially adapted for use during closure of an incision. The retractor comprises a straight shaft, a blade and means for pivotally connecting the blade to the shaft with the blade oriented perpendicularly to the shaft and being free to turn about an axis perpendicular to the shaft. The retractor may further comprise means for telescopically adjusting the length of the shaft and releasably fixing the shaft at the adjusted length. A sole may be formed on the free extremity of the blade most remote from the pivotal connection. The sole is symmetrically formed on the blade and defines surfaces in planes perpendicular to the turning axis of the blade. The surfaces extend equally beyond the thickness of the blade in opposite directions.

DETAILED DESCRIPTION OF PREFERRED EMBODIMENTS

Figure 1:
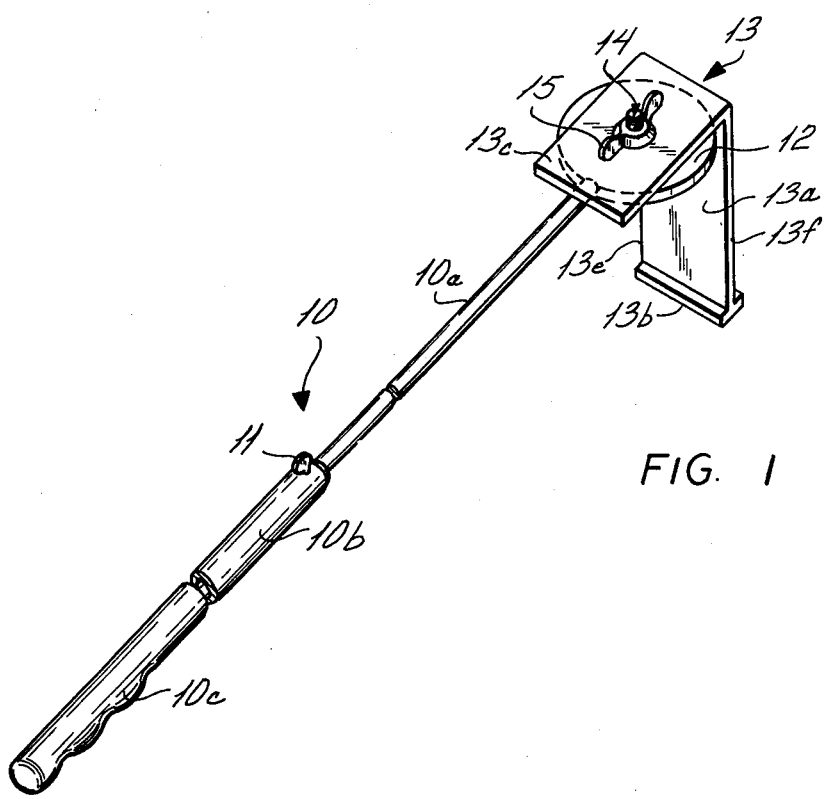
FIG. 1 is an isometric view of a retractor according to the invention.
Figure 2:
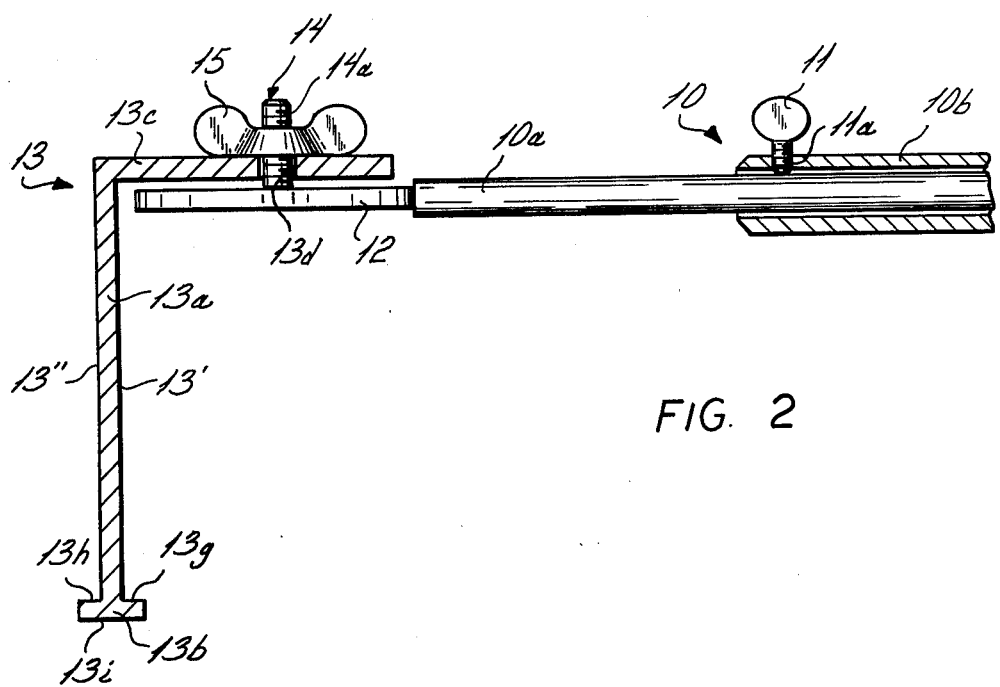
FIG. 2 is a lengthwise cross section of part of the retractor of FIG. 1.

The shaft 10 of the retractor is comprised of a smaller diameter rod 10a received in a larger diameter tubular rod 10b having a handle portion 10c to facilitate gripping. The rod 10a is telescopically received in the tubular rod 10b. By telescoping the rod 10a further into or out of the tubular rod 10b, the total length of the shaft 10 can be adjusted to a length which is optimum for the particular circumstances under which the retractor is being used. Obviously, if desired, the shaft 10 may be constituted of a greater number of telescoping sections. Any conventional means may be provided for locking the telescoping sections at a length to which they are adjusted. One such means is illustrated here. In particular, the retractor is provided with a wing bolt 11 received in a threaded hole in the tubular rod 10b. When it is desired to adjust the amount of telescoping of the rod 10a into the tubular rod 10b, the wing bolt 11 is loosened up and the telescoping is adjusted. Then the wing bolt 11 is twisted into the hole 11a to an extent sufficient that it locks the rod 10a against a portion of the internal wall of the tubular rod 10b.

A flat, disc-shaped bearing 12 is rigidly connected to the distal end of the rod 10a. The retractor blade 13, which is pivotally connected to the bearing 12, is provided with a working portion 13a, including a sole 13b, and a pivot arm portion 13c. A hole 13d is provided centrally through the pivot arm portion 13c. A pivot 14 having threads 14a is integrally connected to the center of the bearing 12. The diameter of the hole 13d is slightly greater than the diameter of the threads 14a on the pivot 14 so that the blade 13 can freely turn about the axis of the pivot 14. It is apparent that the blade can turn quite extensively in either direction, until either side 13e or side 13f of the blade working portion 13a comes into contact with the tubular rod 10a. It is apparent that the exact extent of freedom of movement of the blade 13 will depend on the dimensions of the blade 13 and the diameter of the rod 10a but in all instances will substantially exceed 180° and, in many instances will be 270° or greater. A wing nut 15 holds the blade 13 on the pivot 14. For the purpose of clarity of illustration, in the drawing the pivot arm portion 13c is shown spaced above the bearing 12. In practice, however, the pivot arm portion 13c will generally ride on the bearing 12 and a clearance will exist between the wing nut 15 and the pivot arm portion 13c. If at any time it is desired to secure the blade 13 at a fixed orientation relative to the shaft 10, the wing nut 15 may be tightened down sufficiently that the pivot arm portion of the blade is tightly gripped between the wing nut 15 and the bearing 12. Generally, however, the blade 13 will be left free to turn.

The illustrated retractor is intended to be used by having face 13' of the blade working portion 13a pulled against the structures of the surgical incision or by having face 13" of the blade working portion pushed against the structures of the surgical incision. In this regard, it is noted that the blade working portion 13a is perpendicular to the blade pivot arm portion 13c and, consequently, to the shaft 10. Because the retractor is intended to be used either by pulling or by pushing, the sole 13b, formed on the distal end of the blade 13, and defining surfaces 13g, 13h and 13i in planes perpendicular to the turning axis of the blade 13, is symmetrically disposed on the blade 13 and the surfaces 13g, 13h and 13*i* thereof extend equally beyond the thickness of the blade 13 in opposite directions. The surface 13*g* tends to anchor the blade 13 in the incision when the retractor is being pulled and the surface 13*h* performs the same function when the retractor is being pushed. The surface 13*i* provides a relatively broad, flat surface which will not damage tissue in the incision.

The person using the retractor of the invention can manipulate the retractor while being positioned sufficiently close to the incision so that he is not working blind and sufficiently far from the operator so that he does not interfere with the operator while assisting the operator. Because the blade pivots and can be pushed or pulled, the person using the retractor can readily manipulate it about the incision as the incision is being closed with sutures by the operator.

While the invention has been described by reference to a particular embodiment thereof, it is to be understood that this is intended to illustrate rather than limit the invention and that variations and modificitions obvious to one skilled in the art are intended to be within the scope of the invention as defined by the hereto appended claims.

What I claim is:

1. A hand held surgical retractor comprising a substantially straight shaft, a blade having substantially flat opposed faces, means for pivotally connecting the blade to one end of the shaft with the blade oriented substantially perpendicularly to the shaft and being free to turn about an axis substantially perpendicular to the shaft, the other end of the shaft being free, a handle formed at the free end of the shaft, an extremity of the blade most remote from the pivotal connection being free, and a rigid sole formed on the free extremity of the blade and defining substantially flat surfaces contiguous with and extending substantially perpendicularly from the flat faces of the blade beyond the thickness of the blade in opposite directions.

2. A surgical retractor according to claim 1, in which the sole is symmetrical relative to the blade.

3. A surgical retractor according to claim 1, comprising means for telescopically adjusting the length of the shaft and releasably fixing the shaft at the adjusted length.

4. A surgical retractor according to claim 1, in which the means for pivotally connecting the blade to one end of the shaft comprises an arm portion of the blade integrally formed with the blade and extending substantially perpendicularly to the blade in a plane substantially parallel to said flat surfaces of said sole, means defining at said one end of said shaft a flat bearing surface having an aperture formed therethrough substantially perpendicularly to said bearing surface, said flat bearing surface facing away from said flat surfaces of said sole and being in a plane substantially parallel thereto, a pivot pin connected at one end to and extending at right angles from said bearing surface, the other end of said pivot pin being free, said free end of said pivot pin being received through said aperture, said aperture being of larger diameter than said pin, and means for releasably locking said arm portion of said blade against said bearing surface.

5. A surgical retractor according to claim 4, in which said pivot pin has screw threads formed thereon and said releasable locking means comprises a wing nut which engages the threads on said pivot pin.

* * * * *